United States Patent [19]

Sander et al.

[11] Patent Number: 5,713,903
[45] Date of Patent: Feb. 3, 1998

[54] ORTHOPEDIC FASTENER

[75] Inventors: Thomas W. Sander, Newtown; Daniel R. Lee, Norwalk; Robert Gangnath, Monroe, all of Conn.

[73] Assignee: United States Surgical Corporation, Norwalk, Conn.

[21] Appl. No.: 777,117

[22] Filed: Dec. 30, 1996

Related U.S. Application Data

[63] Continuation of Ser. No. 586,303, Jan. 17, 1996, which is a continuation of Ser. No. 439,719, May 12, 1995, abandoned, which is a continuation of Ser. No. 367,662, Jan. 3, 1995, abandoned, which is a continuation of Ser. No. 38,551, Mar. 26, 1993, abandoned, which is a continuation of Ser. No. 673,953, Mar. 22, 1991, abandoned.

[51] Int. Cl.$^6$ ............................................. A61B 17/58
[52] U.S. Cl. ........................... 606/72; 606/60; 606/67
[58] Field of Search ............................. 606/53, 60, 72, 606/73, 61, 62, 63, 64, 65, 66, 67, 68, 76, 77; 623/11, 22, 23

[56] References Cited

U.S. PATENT DOCUMENTS

| 2,121,193 | 6/1938 | Hanicke | 128/92 |
|---|---|---|---|
| 2,381,050 | 8/1945 | Hardinge . | |
| 2,489,870 | 11/1949 | Dzus | 606/73 |

(List continued on next page.)

FOREIGN PATENT DOCUMENTS

| 0019782 | 12/1980 | European Pat. Off. . | |
|---|---|---|---|
| 0077868 | 5/1983 | European Pat. Off. . | |
| 0124489 | 11/1984 | European Pat. Off. . | |
| 230937A | 1/1987 | European Pat. Off. . | |
| 0232049 | 8/1987 | European Pat. Off. . | |
| 0241240 | 10/1987 | European Pat. Off. . | |
| 0238223 | 6/1988 | European Pat. Off. . | |
| 0270704 | 7/1989 | European Pat. Off. . | |
| 0376641 | 7/1990 | European Pat. Off. . | |
| 0409364 | 1/1991 | European Pat. Off. . | |
| 0464479 | 1/1992 | European Pat. Off. . | |
| 0464480 | 1/1992 | European Pat. Off. . | |
| 0465910 | 1/1992 | European Pat. Off. . | |
| 0502509 | 9/1992 | European Pat. Off. . | |
| 0504915 | 9/1992 | European Pat. Off. . | |
| 0588671 | 3/1994 | European Pat. Off. . | |
| 739089 | 1/1933 | France | 606/73 |
| 2622430A | 9/1987 | France . | |
| 2622430 | 5/1989 | France . | |
| 3445738 | 6/1986 | Germany . | |
| 3509417 | 9/1986 | Germany | 606/73 |
| 8633339 | 4/1987 | Germany . | |
| 4106823 | 6/1992 | Germany . | |
| 584855 | 12/1977 | U.S.S.R. | 606/73 |

(List continued on next page.)

OTHER PUBLICATIONS

Arthroscopy Equipment and Supplies (Instrument Makar, Inc.).
The Complete Arthrex Information System.
Mitek G II Anchor.
Mitek Anchor System.
Mitek Quick Anchor.
Statak Soft Tissue Attachment Device.
Tag Tissue Anchor Guide.
Tag Tissue Anchor Rod Style.
Tag Tissue Anchor Wedge Style.
Rivet Joints in Aluminium Structural Components.
Special Blind Rivets.
Arthroscopy Equipment and Supplies brochure of Instrument Makar, Inc.
Ligament Screw System brochure by Biomet Inc.

*Primary Examiner*—Sam Rimell
*Assistant Examiner*—Robert V. Racunas

[57] ABSTRACT

Soft tissue is secured to bone with a surgical fastener having expandable legs. The surgical fastener is implanted into a predrilled hole in the bone and the legs are expanded by pulling a slidable pin with a flared distal end. The pin includes a breakaway notch. The fastener may be fabricated from resorbable material and may be implanted arthroscopically.

33 Claims, 5 Drawing Sheets

U.S. PATENT DOCUMENTS

| | | | |
|---|---|---|---|
| 2,490,364 | 12/1949 | Livingston . | |
| 2,699,774 | 1/1955 | Livingston . | |
| 3,759,257 | 9/1973 | Fischer et al. . | |
| 3,760,802 | 9/1973 | Fischer et al. . | |
| 3,779,239 | 12/1973 | Fischer et al. . | |
| 3,782,374 | 1/1974 | Fischer . | |
| 3,805,775 | 4/1974 | Fischer et al. . | |
| 3,846,846 | 11/1974 | Fischer | 606/72 X |
| 3,910,281 | 10/1975 | Kletschka et al. | 128/335 |
| 3,958,488 | 5/1976 | Fischer | 85/77 |
| 3,986,504 | 10/1976 | Avila | 128/92 |
| 4,006,747 | 2/1977 | Kronenthal et al. | 128/335 |
| 4,013,071 | 3/1977 | Rosenberg | 128/92 B |
| 4,091,806 | 5/1978 | Aginsky . | |
| 4,204,531 | 5/1980 | Aginsky . | |
| 4,227,518 | 10/1980 | Aginsky . | |
| 4,236,512 | 12/1980 | Aginsky . | |
| 4,244,370 | 1/1981 | Furlow et al. | 128/303 R |
| 4,259,072 | 3/1981 | Hirabayashi et al. | 433/173 |
| 4,262,665 | 4/1981 | Roalstad et al. | 128/92 BC |
| 4,275,717 | 6/1981 | Bolesky | 128/92 BC |
| 4,309,137 | 1/1982 | Tanaka et al. | 411/45 |
| 4,339,217 | 7/1982 | Lacey . | |
| 4,351,069 | 9/1982 | Ballintyn et al. | 3/1.912 |
| 4,409,974 | 10/1983 | Freedland | 128/92 B |
| 4,414,967 | 11/1983 | Shapiro | 128/92 B |
| 4,453,539 | 6/1984 | Raftopoulos et al. | 128/92 BC |
| 4,454,875 | 6/1984 | Pratt et al. . | |
| 4,456,005 | 6/1984 | Lichty | 128/92 A |
| 4,474,517 | 10/1984 | Navoczynski | 411/45 |
| 4,483,678 | 11/1984 | Nishio et al. | 433/201 |
| 4,519,100 | 5/1985 | Wills et al. | 3/1.9 |
| 4,519,735 | 5/1985 | Mächtle . | |
| 4,520,511 | 6/1985 | Gianezio et al. | 3/1.913 |
| 4,539,981 | 9/1985 | Tunc | 128/92 B |
| 4,542,539 | 9/1985 | Rowe, Jr. et al. | 623/16 |
| 4,550,448 | 11/1985 | Kenna | 623/16 |
| 4,550,449 | 11/1985 | Tunc | 623/16 |
| 4,570,623 | 2/1986 | Ellison et al. . | |
| 4,586,502 | 5/1986 | Bedi et al. | 128/334 R |
| 4,590,928 | 5/1986 | Hunt et al. . | |
| 4,590,930 | 5/1986 | Kurth et al. | 128/92 BC |
| 4,596,503 | 6/1986 | Mirsberger et al. | 411/32 |
| 4,599,085 | 7/1986 | Riess et al. | 623/16 |
| 4,612,923 | 9/1986 | Kronenthal | 128/92 R |
| 4,632,100 | 12/1986 | Somers et al. | 128/92 |
| 4,640,271 | 2/1987 | Lower | 128/92 YF |
| 4,653,486 | 3/1987 | Coker | 128/92 YF |
| 4,655,777 | 4/1987 | Dunn et al. | 623/16 |
| 4,656,806 | 4/1987 | Leibhard et al. . | |
| 4,669,473 | 6/1987 | Richards et al. | 128/334 |
| 4,681,590 | 7/1987 | Tansey | 623/23 |
| 4,711,232 | 12/1987 | Fischer et al. . | |
| 4,713,076 | 12/1987 | Draenert | 623/16 |
| 4,716,893 | 1/1988 | Fischer et al. . | |
| 4,738,255 | 4/1988 | Goble et al. | 128/92 YF |
| 4,741,330 | 5/1988 | Hayhurst | 128/92 YF |
| 4,759,670 | 7/1988 | Linder et al. | 411/43 |
| 4,760,843 | 8/1988 | Fischer et al. . | |
| 4,767,248 | 8/1988 | Pratt | 411/45 |
| 4,776,328 | 10/1988 | Frey et al. | 128/92 VT |
| 4,776,329 | 10/1988 | Treharne . | |
| 4,778,468 | 10/1988 | Hunt et al. | 623/16 |
| 4,787,378 | 11/1988 | Sodhi . | |
| 4,790,303 | 12/1988 | Steffee | 128/924 M |
| 4,790,304 | 12/1988 | Rosenberg . | |
| 4,793,335 | 12/1988 | Frey et al. | 606/73 |
| 4,796,612 | 1/1989 | Reese | 128/92 YF |
| 4,806,053 | 2/1989 | Herb . | |
| 4,818,163 | 4/1989 | Bereiter et al. . | |
| 4,828,562 | 5/1989 | Kenna | 623/13 |
| 4,834,752 | 5/1989 | Van Kampen . | |
| 4,861,197 | 8/1989 | Calandra, Jr. . | |
| 4,870,957 | 10/1989 | Goble et al. . | |
| 4,871,289 | 10/1989 | Choiniere . | |
| 4,895,148 | 1/1990 | Bays et al. | 606/213 |
| 4,898,156 | 2/1990 | Gatturna et al. | 606/72 |
| 4,898,505 | 2/1990 | Froehlich . | |
| 4,899,743 | 2/1990 | Nicholson et al. | 606/139 |
| 4,921,383 | 5/1990 | Fischer . | |
| 4,927,421 | 5/1990 | Goble et al. . | |
| 4,938,760 | 7/1990 | Burton et al. | 600/29 |
| 4,946,468 | 8/1990 | Li | 606/232 |
| 4,963,144 | 10/1990 | Huene . | |
| 4,968,315 | 11/1990 | Gatturna | 606/72 |
| 4,969,887 | 11/1990 | Sodhi | 606/67 |
| 4,969,892 | 11/1990 | Burton et al. | 606/218 |
| 4,976,680 | 12/1990 | Hayman et al. | 600/7 |
| 4,976,715 | 12/1990 | Bays et al. | 606/77 |
| 4,988,351 | 1/1991 | Paulos et al. | 606/75 X |
| 5,002,550 | 3/1991 | Li | 606/139 |
| 5,011,473 | 4/1991 | Gatturna | 604/51 |
| 5,013,316 | 5/1991 | Goble et al. | 606/72 |
| 5,015,250 | 5/1991 | Foster | 606/147 |
| 5,036,862 | 8/1991 | Pohndorf | 128/784 |
| 5,037,422 | 8/1991 | Hayhurst et al. | 606/72 |
| 5,041,129 | 8/1991 | Hayhurst et al. | 606/232 |
| 5,046,513 | 9/1991 | Gatturna et al. | 128/898 |
| 5,053,047 | 10/1991 | Yoon | 606/223 |
| 5,076,746 | 12/1991 | Fischer et al. . | |
| 5,078,730 | 1/1992 | Li et al. | 606/228 |
| 5,080,543 | 1/1992 | Murphy | 411/60 |
| 5,084,050 | 1/1992 | Draenert | 606/77 |
| 5,085,545 | 2/1992 | Takahashi | 411/45 |
| 5,085,661 | 2/1992 | Moss | 606/139 |
| 5,100,405 | 3/1992 | McLaren | 606/72 |
| 5,100,417 | 3/1992 | Cerier et al. | 606/139 |
| 5,102,421 | 4/1992 | Anspach, Jr. | 606/232 |
| 5,122,133 | 6/1992 | Evans | 606/73 |
| 5,129,906 | 7/1992 | Ross et al. | 606/77 |
| 5,154,719 | 10/1992 | Cotrel | 606/73 |
| 5,209,753 | 5/1993 | Biedermann et al. | 606/72 |
| 5,224,946 | 7/1993 | Hayhurst et al. | 606/72 |
| 5,236,445 | 8/1993 | Hayhurst et al. | 606/232 |
| 5,246,441 | 9/1993 | Ross et al. | 606/53 |
| 5,258,016 | 11/1993 | DiPoto et al. | 606/239 |
| 5,268,001 | 12/1993 | Nicholson et al. | 606/72 |
| 5,480,403 | 1/1996 | Lee et al. | 606/72 |

FOREIGN PATENT DOCUMENTS

| | | | |
|---|---|---|---|
| 8603666 | 7/1986 | U.S.S.R. . | |
| 2084468 | 4/1982 | United Kingdom . | |
| 2199914 | 7/1988 | United Kingdom . | |
| 2266246 | 10/1993 | United Kingdom . | |
| WO8504568 | 10/1985 | WIPO . | |
| 0232049 | 8/1987 | WIPO . | |
| WO8901767 | 3/1989 | WIPO . | |
| 8909030 | 9/1989 | WIPO | 606/73 |
| 8910096 | 11/1989 | WIPO . | |
| 9204874 | 4/1992 | WIPO . | |
| 9308747 | 5/1993 | WIPO . | |

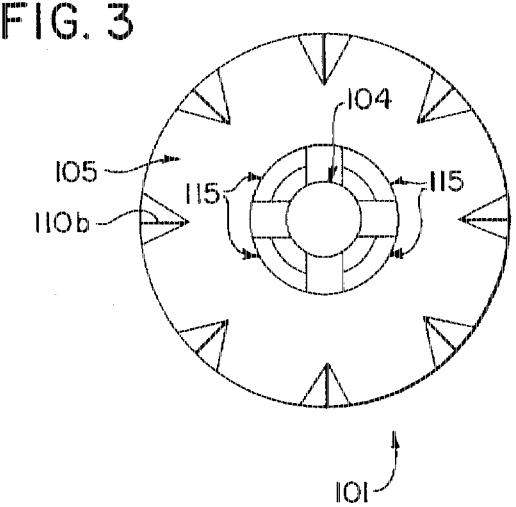
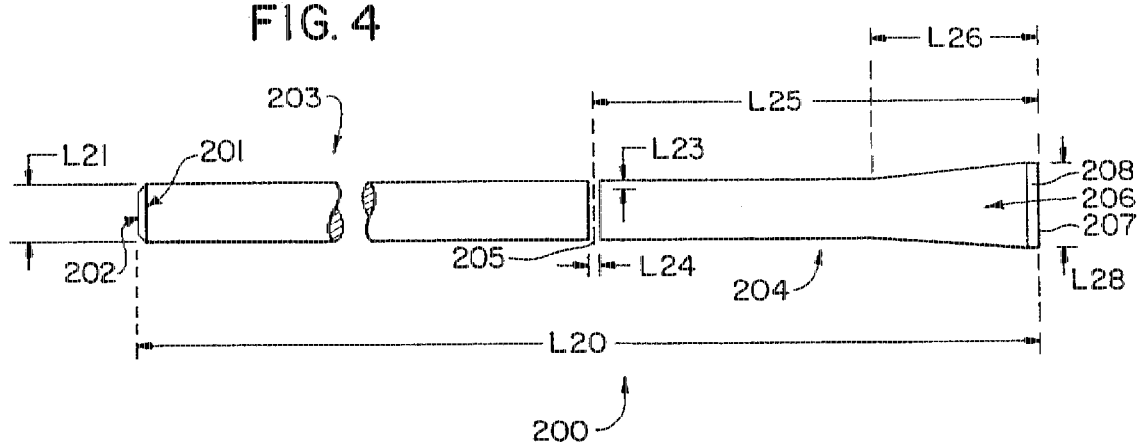
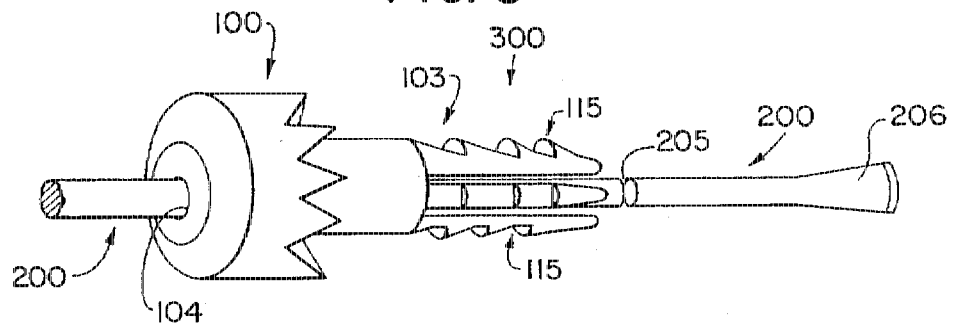

ORTHOPEDIC FASTENER

This is a continuation of co-pending U.S. application Ser. No. 08/586,303, filed on Jan. 17, 1996, which is a continuation of 08/439,719, filed on May 12, 1995, now abandoned, which is a continuation of Ser. No. 08/367,662, filed on Jan. 3, 1995, now abandoned, which is a continuation of Ser. No. 08/038,551, filed on Mar. 26, 1993, now abandoned, which is a continuation of Ser. No. 07/673,953, filed on Mar. 22, 1991, now abandoned.

BACKGROUND OF THE INVENTION

1. Field of the Invention

This invention relates to a surgical fastener which may be anchored into bone, and more particularly to a surgical fastener for fastening soft tissue to bone.

2. Background of the Art

Surgical bone fasteners are known in the art. Also known are devices for anchoring soft tissue, such as ligament or tendon, to bone.

Generally, these devices fall into two categories: (1) staple type systems, or (2) screw and washer type systems.

The first of these types is illustrated in U.S. Pat. Nos. 4,454,875 and 4,570,623 which show metal staples with spikes on the underside of the crosspiece to secure ligaments.

The second of these types are available as screw-washer combinations wherein the screw is fabricated from a surgically suitable metal, such as titanium, and is of self-tapping design. The washer has distal pointing spikes and a central aperture through which the screw is disposed.

Other ligament anchor systems are disclosed in U.S. Pat. Nos. 4,927,421 and 4,870,957.

The prior known devices for securing ligaments possess several disadvantages. Staples, which are meant to be hammered into bone, must be made of a strong material, such as metal. This precludes the use of bioabsorbable polymers as fabrication material for the fasteners (staples). Additionally, hammering staples into the bone can be time consuming. Screw devices are also confined to metals as materials of fabrication, especially self-tapping screws. These screw devices further require a hole in the bone to be drilled which may have to be tapped, a procedure which is time consuming. Prior staples and screw ligament fasteners which are made of metal are permanently implanted into the body unless a second surgical operation is performed to remove them. In either case, implantation of metal devices does not allow for transfer of stress back to the bone/soft tissue junction as the healing proceeds. This, in turn, may slow down or impede the healing process.

Furthermore, the metal screws and staples may actually migrate from their original insertion site over a period of time. Even though healing may have occured, a screw or staple that has backed out can be palpated and may cause pain to the patient. These screws and staples can even migrate into the joint space creating significant damage to articular cartilage and other structures.

The need therefore exists for a fastener for securing tissue to bone which will have sufficient initial anchorage strength as well as allow for gradual load sharing to provide full repair and restoration of function of the tissue and bone. The need further exists for such a device which is easily and rapidly anchored into the tissue does not harmfully migrate from its original position.

SUMMARY OF THE INVENTION

A surgical fastener for securing soft tissue to bone is provided herein which facilitates the insertion as well as enhances healing of the tissue and bone. The surgical fastener comprises (a) a rivet having an axial bore, distal locking means for frictionally engaging the bone to secure the rivet thereto, and a proximal head portion preferably having means for holding soft tissue; and, (b) a pin receivable into said bore and proximally slidable therein, said pin having means for activating said rivet locking means in response to proximal movement of said pin within said bore. The locking means preferably includes at least two radially expandable barbed legs projecting distally from the rivet. The fastener may be fabricated from a resorbable material such as polymers of glycolide, lactide, caprolactone, polyorthoesters, polydioxanone, trimethylene carbonate, polyethylene oxide and mixtures and copolymers thereof.

The means for holding soft tissue may comprise a plurality of soft tissue engaging barbs projecting distally from the rivet head.

The means for activating the rivet locking means preferably comprises a flared portion at the distal end portion of the pin, the flared portion having a diameter greater than the diameter of the bore and being engageable with the inner surface of the rivet legs to expand the legs radially outward.

The pin may include a circumferential notch disposed between a proximal portion and a distal portion. The notch provides means for separating the proximal portion from the distal portion when a pulling force of sufficient magnitude is applied to the proximal portion. The pin may also include a plurality of ribs.

The present invention also provides a method for securing soft tissue to bone, comprising (a) drilling a hole into the bone for receiving a surgical fastener; (b) inserting the above described surgical fastener into said hole; (c) placing the fastener so as to hold the soft tissue in contact with said bone; and (d) moving the pin proximally to activate said locking means.

The method may further include the step of applying to the proximal portion of said pin a pulling force of magnitude sufficient to break the pin at said notch.

BRIEF DESCRIPTION OF THE DRAWINGS

FIGS. 1, 2, and 3 illustrate, respectively, a side elevation view, a cross-sectional view, and an end view of the rivet portion of the surgical fastener of the present invention;

FIG. 4 illustrates an elevational view of the pin portion of the surgical fastener of the present invention;

FIG. 5 illustrates a perspective view of the surgical fastener of the present invention showing the pin portion inserted through the rivet portion;

DETAILED DESCRIPTION OF A PREFERRED EMBODIMENT

The orthopedic fastener of the present invention comprises two elements: (1) a rivet with a soft tissue-engaging barbed head and an integral sleeve possessing expandable legs, and (2) a rod-shaped setting pin terminating in a flared section and optionally possessing a circumferential groove defining a breakaway point when the retraction force applied to the pin exceeds the pin's tensile strength. When the setting pin is retracted through the sleeve of the rivet, its flared section forces the legs of the sleeve open, thereby compressing the legs against bone into which the rivet has previously been inserted, and thus anchoring the rivet firmly in place.

Figure 1:
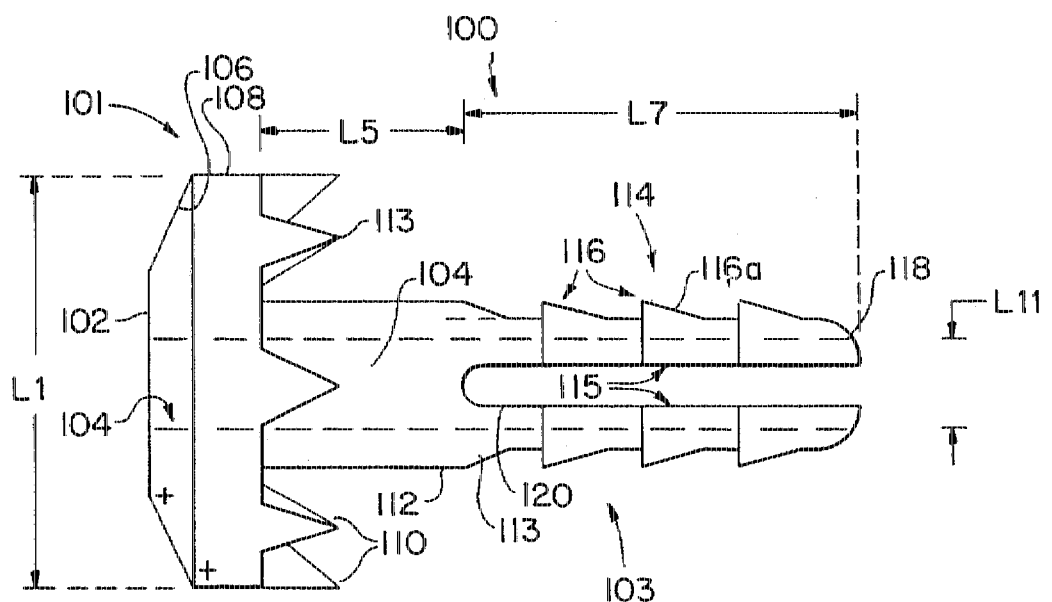

Referring now to FIG. 1, rivet 100 includes a head portion 101 at the proximal end and a sleeve portion 103 extending distally from head portion 101. A central (axial) bore 104 extends longitudinally through the rivet 100, i.e. through head portion 101 and sleeve portion 103, to allow for passage of pin 200 described below.

Figure 2:
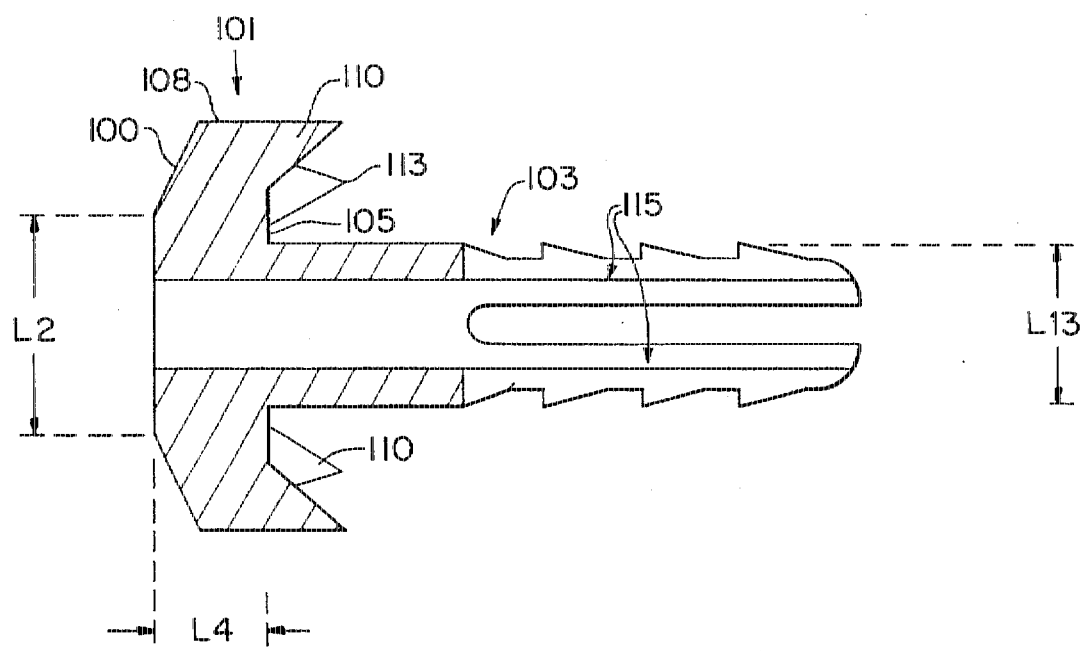

Head portion 101 includes a circular flat proximal outer surface 102 adapted to receive a suitable instrument for driving the rivet through the tissue and bone. Sloped surface 106 joins proximal outer surface 102 to peripheral cylindrical surface 108 as shown in FIGS. 1 and 2. Extending from the internal or distal surface 105 of rivet head portion 101 are a plurality of barbs 110 having pointed tips 113. As shown in FIGS. 1 and 3, the barbs 110 are spaced apart from each other and extend from the circumferential periphery of the rivet head portion 101. Alternately, one or more of the barbs can be positioned inwardly of the circumferential portion of the head portion 101. The barbs 101 are configured and dimensioned to facilitate penetration into the tissue as well as improve anchorage of the tissue after insertion. The barbs are shown substantially triangular in shape and substantially equally spaced part but other configurations and arrangements are contemplated which could achieve the aforementioned functions.

Sleeve portion 103 of rivet 100 has a substantially cylindrical portion 112 and a distal portion 114 having a plurality of spaced apart legs 115 which extend distally from cylindrical portion 112. Legs 115, separated by notches 120, are flexible and resilient for the reasons which will become apparent from the discussion below. Each leg 115 preferably includes a plurality of outwardly extending barbs 116 shown as substantially triangular shaped. However, other shaped barbs can clearly be utilized. Barbs 116 include an inclined distal surface 116a which is inclined at an angle from the axial orientation of the sleeve 103. Barbs 116 are configured and dimensioned to anchor the rivet 100 in the bone and to prevent the device from pulling out (i.e. proximal movement of the rivet). Sleeve 103 terminates at curved distal end 118.

In the illustrated embodiment, four spaced apart legs 115 are provided. Alternately, a fewer or larger number of legs could be provided as long as they have sufficient flexibility and resiliency. In still another alternate embodiment, notches 120 can be eliminated so that the distal portion of sleeve 103 is tubular and composed of a suitable material that will allow expansion upon movement of the pin. In this embodiment the central bore of the head portion and proximal sleeve portion will likewise extend through the distal sleeve portion.

Referring now to FIG. 4, rod-shaped setting pin comprises a shaft 200 having a proximal section 203 and a distal section 204. Proximal section has a slightly tapered proximal end 202 tapering at an angle to surface 201. Distal section 204 has a flared portion 206 extending distally outwardly and terminating in distal end surface 207. The flared portion 206 has a diameter L28 greater than the diameter of the region formed between the spaced apart legs 115 (L11 of FIG. 1), to thereby cause outward deflection of legs 115 in the manner described below.

A circumferential notch or groove 205 is formed in shaft 200 between distal section 204 and proximal section 203. The notch 205 is configured to allow breaking of the pin, i.e. separation of the distal and proximal sections 204, 203, when sufficient retraction force is applied. The notch 205 can be positioned at any desired location in shaft 200.

The pin 200 and rivet 100 of the present invention are assembled into orthopedic fastener 300 as shown in FIG. 5. The pin 200 is slidably disposed through axial aperture or bore 104 with flared end 206 protruding distally from the legs 115 of rivet 100.

Figure 6:
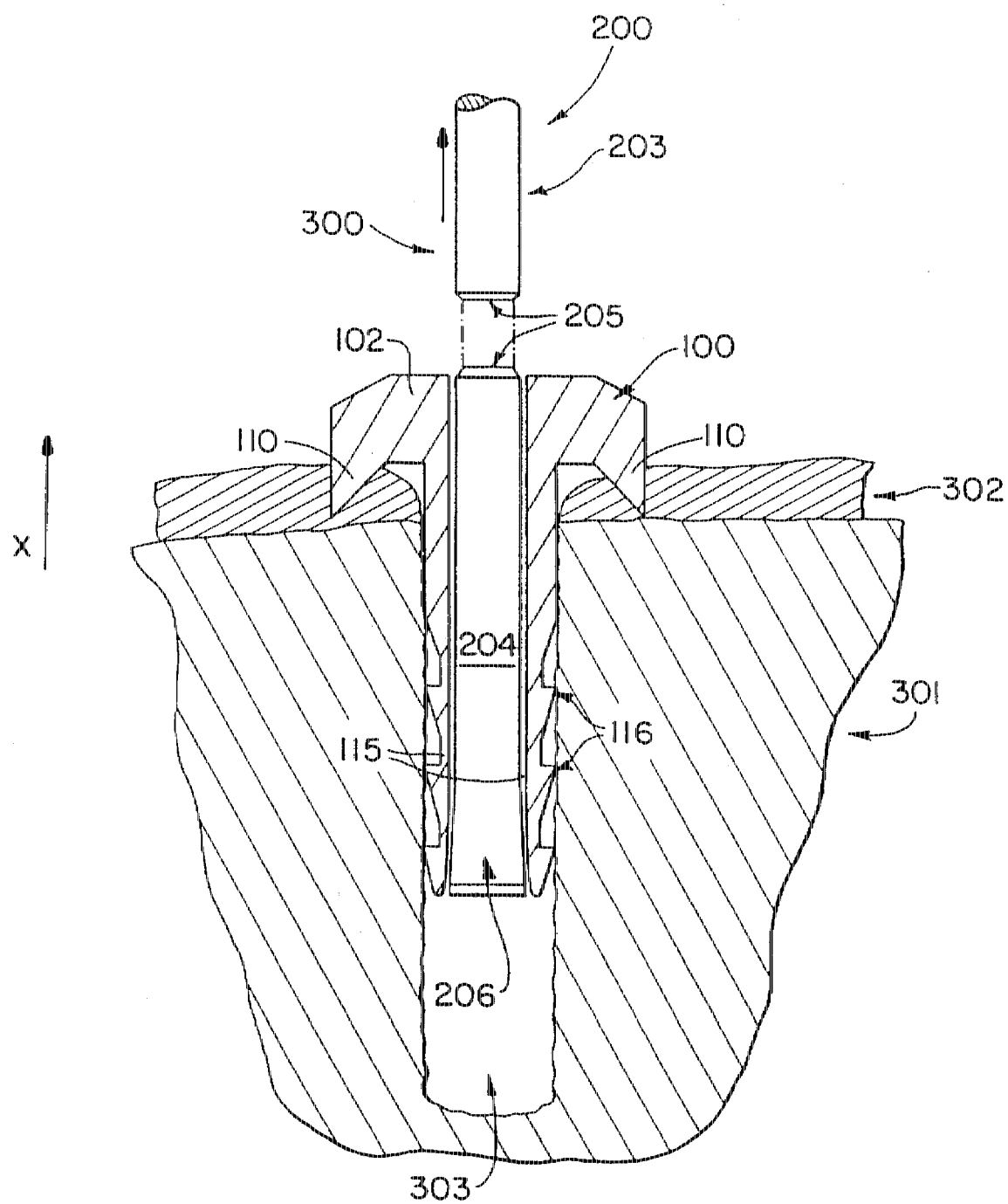
FIG. 6 illustrates the surgical fastener of the present invention implanted into bone.

To use the orthopedic fastener, a small incision or hole is made in the tissue and a hole is predrilled into the bone of sufficient diameter to accommodate the orthopedic fastener. Referring to FIG. 6, the orthopedic fastener 300 is inserted into the predrilled hole 303 in bone 301. The orthopedic fastener 300 is pressed in such that barbs 110 bite into soft tissue 302 to hold tissue 302 in close proximity to the surface of bone 301. The pin 200 is then pulled proximally by the surgeon (in the direction of arrow x) thereby urging flared section 206 through aperture 204 and between legs 115. The flared section 206 engages the inner surface of legs 115 and forces legs 115 radially outward so that barbs 116 bite into the side walls of predrilled hole 503 to hold the rivet firmly in place by increased friction. When the pulling force exerted by the surgeon on the proximal portion 203 of pin 200 exceeds the tensile strength of the pin, the pin 200 breaks at the notch 205 leaving a surface approximately flush with surface 102 of the rivet. The proximal portion 203 of the pin may then be discarded leaving the remainder of the orthopedic fastener in place to hold down soft tissue 302 for a time sufficient to promote healing and attachment of the soft tissue 302 to bone 301.

Figure 7A:
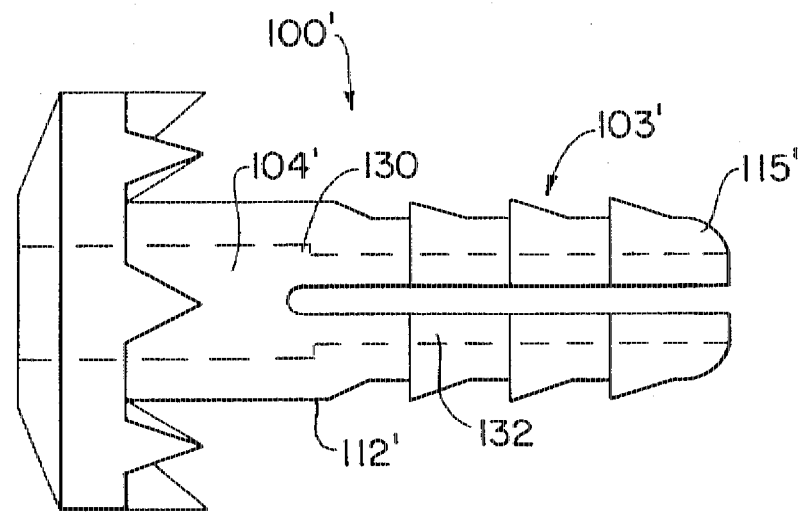
FIGS. 7A and 7B illustrate, respectively, a side elevation view and a cross-sectional view of an alternate embodiment of the rivet portion of the present invention.
Figure 7B:
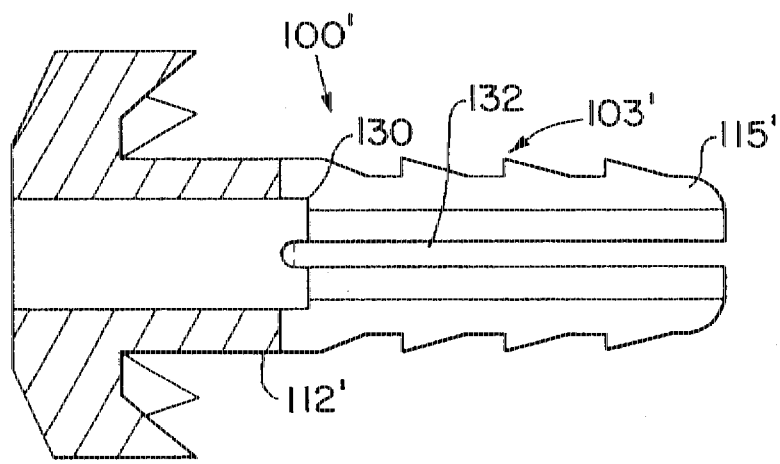
Figure 8:
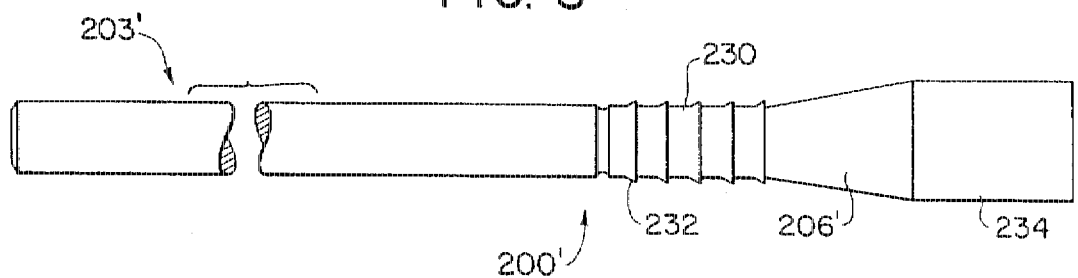
FIG. 8 illustrates an alternate embodiment of the pin portion of the present invention.

FIGS. 7A, 7B and 8, illustrate an alternate embodiment of the present invention to improve retention of the pin within the rivet. Bore 104' of rivet 100' includes a narrow portion 132 which begins at edge 130 inside cylindrical portion 112' of sleeve portion 103' and terminates at the distal portion of the legs 115'. Pin 200' has a plurality of outwardly extending ribs 230 with surfaces 232 inclined towards proximal section 203'. Ribs 230 engage edge 130 of rivet 100' to help hold pin 200' in its initial position and to prevent pin 200' from sliding distally as the pin 200' is pulled proximally in the manner described above.

Figure 10:
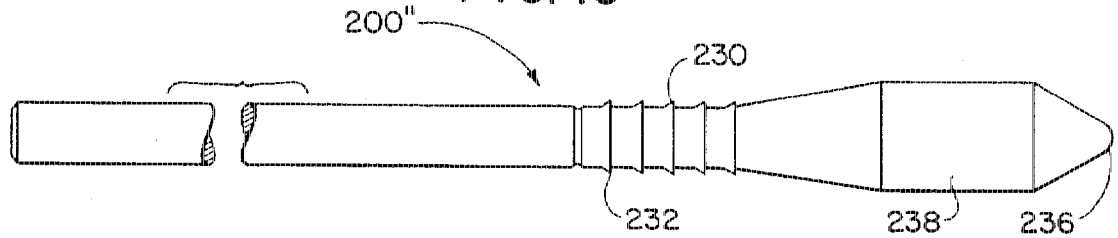
FIG. 10 illustrates an alternate embodiment of the proximal portion of the pin portion of the present invention.

Pin 200' may also include a distal end portion 234 of substantially uniform diameter disposed distally of flared section 206'. This distal end portion 234 can also be formed distally of flared section 206 of pin 200 illustrated in FIG. 4. In an alternate embodiment shown in FIG. 10, distal end portion 238 of pin 200" has a rounded conical tip 236 to facilitate entry of pin 200" into the hole in the bone.

Figure 9:
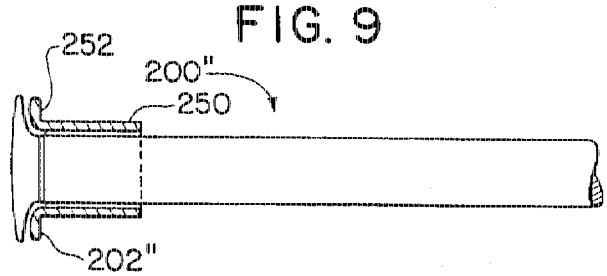
FIG. 9 illustrates an alternate embodiment of the proximal portion of the pin portion of the present invention.

To facilitate gripping the pin when pulling it proximally to spread legs 115 apart, a metal eyelet 250, having a flared portion 252 as shown in FIG. 9, may be attached to the outer surface of pin 200" directly below rim 254 formed at the proximal end 202".

If the orthopedic fastener is fabricated from a resorbable (bioabsorbable) material, it will stay in place in the bone for a limited period of time without the necessity for a separate surgical operation to remove it. Thereafter, the resorbable orthopedic fastener will be gradually decomposed and assimilated by the body. Examples of resorbable materials which can be utilized include homopolymers or copolymers of lactide, glycolide, polydioxonone, trimethylene, carbonate, polyorthoesters, polyethylene oxide or other bioabsorbable polymer materials or blends of these respective polymers. One preferred material is made of a copolymer of lactide and glycolide made from approximately 18% m glycolide and 82% m lactide.

An advantageous feature of the present invention is that it is only necessary to have a predrilled hole in the bone, and a small incision in the surrounding tissue. The hole does not have to be tapped and the orthopedic fastener does not have to be hammered into place. Once set, the orthopedic fastener of the present invention is held in place by friction. This friction holds the fastener secure under both shear loading and pull-out force. However, this friction holding feature is not activated during insertion, which makes insertion of the fastener into the predrilled hole easy. Thus, the orthopedic fastener of the present invention has a friction locking feature which may be in an inactivated condition (before and during insertion of the operation site), and an activated condition (after being set by retraction of the pin 200).

The orthopedic fastener of the present invention has the further beneficial features of being more easily applied with arthroscopic procedures, for example, through a narrow cannula. The orthopedic fastener of the present invention may also advantageously be made of resorbable polymers, as stated above, thereby allowing gradual load sharing to the repaired tissue over a period of time. Resorbability also eliminates the drawbacks associated with migration of permanent, e.g. metal, fasteners.

The dimensions of the rivet and pin will vary depending on its uses. Examples of some dimensions are set forth below. These dimensions provide only an example of the numerous sizes of the fasteners which can be utilized. Therefore, it should be understood that the following example of the present invention illustrates only possible dimensions of the fasteners, and the fastener of the present invention is in no way limited to these dimensions. Reference to FIGS. 1–4 will assist in understanding the dimensions set forth below.

Diameter L1 (FIG. 1) of head portion 101 of rivet 100 ranges from about 0.295 to 0.305 inches; length L5 of the cylindrical portion 112 ranges from about 0.145 to 0.155 inches; and length L7 of the distal portion 114 measures from about 0.295 to about 0.305 inches. The diameter L11 of the area between the legs 115 measures from about 0.065 to about 0.068 inches. The diameter L13 (FIG. 2) of cylindrical portion 112 ranges from about 0.113 to 0.122 inches. The width L4, of head portion 101, excluding barbs 110 is about 0.078 to 0.082 inches. The overall length L20 of pin 200 (FIG. 4) ranges from about 1.498 to 1.502 inches, with the length L25 of distal portion 204 measuring about 0.518 to 0.522 inches and length L26 of flared portion 206 measuring about 0.148 to about 0.152 inches. Diameter L28 of distal end 207 is about 0.091 inches to about 0.093 inches.

In another example, diameter L13 of cylindrical portion 112 ranges from about 0.138 to 0.142 inches, length L20 of pin 200 ranges from about 1.638 to 1.642 inches, length L25 ranges from 0.439 to 0.441 inches, and diameter L28 is about 0.109 to 0.111 inches.

It will be understood that the foregoing is only illustrative of the present invention and that various modifications can be made by those skilled in the art without departing from the scope and spirit of the present invention.

What is claimed is:

1. A surgical fastener for securing soft tissue to bone, which comprises:
   a) a rivet having an axial bore, distal locking means for frictionally engaging the bone to secure the rivet thereto, and a proximal head portion;
   b) a pin receivable into said bore and proximally slidable therein, said pin having a proximal shaft portion, and a distal portion for activating said rivet locking means in response to proximal movement of said pin within said bore, said distal portion being flared with progressively greater diameter in the distal direction,
      said rivet locking means being movable between an inactivated configuration and an activated configuration, and said pin having an end portion distal to said rivet locking means when said rivet locking means is in said inactivated configuration; and
   c) indexing means for preventing distal movement of said pin relative to said rivet when said pin has been moved within said bore to any one of several discrete positions relative to said rivet, said indexing means comprising
      i) a plurality of longitudinally spaced apart circumferential ridges positioned along said proximal portion of said pin, each ridge having an inclined proximal surface and a flat distal surface extending radially outward, and
      ii) a flat proximally facing stop wall positioned in said rivet, said distal surface of each said ridge being resiliently engageable with said proximally facing stop wall to prevent distal movement of said pin relative to said rivet once said ridge is moved proximal to said stop wall, said inclined proximal surface of each said ridge permitting further proximal movement of said pin within said bore.

2. The fastener of claim 1, wherein said locking means comprises at least two radially expandable legs projecting distally from said rivet.

3. The fastener of claim 2 wherein said legs have barbs for engaging bone.

4. The fastener of claim 1 wherein said fastener is fabricated from a resorbable material.

5. The fastener of claim 4 wherein said resorbable material comprises a polymer selected from the group consisting of polymers of lactide, glycolide, caprolactone, polydioxanone, trimethylene carbonate, polyorthoesters, polyethylene oxide or other resorbable polymer materials or blends of these respective polymers.

6. The fastener of claim 1 wherein said head portion is integral to said rivet, said fastener further comprising a plurality of tissue engaging barbs integral with said head portion, said barbs projecting distally from said head portion.

7. The fastener of claim 1 wherein said shaft portion has a substantially unchanging cross-section throughout its length.

8. The fastener of claim 1 wherein said flared portion is engageable with an inner surface of said legs to expand said legs radially outward.

9. The fastener of claim 8 wherein said flared portion has a diameter greater than the diameter of said bore.

10. The fastener of claim 1 wherein said pin includes a circumferential notch defining a proximal breakaway portion and a distal breakaway portion, said notch providing a breaking means for separating said proximal breakaway portion from said distal breakaway portion when a pulling force of sufficient magnitude is applied to said proximal breakaway portion.

11. The fastener of claim 1 wherein said stop wall is positioned adjacent said bore.

12. A surgical fastener for securing soft tissue to bone, which comprises:
   a) a rivet having an axial bore, distal locking means for frictionally engaging the bone to secure the rivet thereto, and a proximal head portion; and, b) a pin receivable into said bore and proximally slidable therein, said pin having means for activating said rivet locking means in response to proximal movement of said pin within said bore, wherein said means for activating the rivet locking means comprises a flared portion at the distal end portion of said pin, and said pin further comprises an eyelet positioned over its proximal end to facilitate gripping of said pin.

13. The fastener of claim 1 wherein said flared portion is disposed at the distalmost end of said pin.

14. The fastener of claim 1 wherein said pin further comprises a portion of substantially uniform diameter disposed in proximity to said flared portion.

15. The fastener of claim 1, wherein said pin has portion has a rounded conical tip at the distal end.

16. A method for securing soft tissue to bone, comprising:
   A) drilling a hole into the bone for receiving a surgical fastener;
   B) inserting a surgical fastener into said hole, said surgical fastener comprising:
      a) a rivet having an axial bore, distal locking means for frictionally engaging the bone to secure the rivet thereto, and a proximal head portion having means for holding soft tissue; and
      b) a pin receivable into said bore and proximally slidable therein, said pin having a proximal portion with a substantially unchanging cross-section throughout the length of said proximal portion, and a distal portion for activating said rivet locking means in response to proximal movement of said pin within said bore, said distal portion having a flared portion with progressively greater diameter in the distal direction,
         said rivet locking means being movable between an inactivated configuration and an activated configuration, and said pin having an end portion distal to said rivet locking means when said rivet locking means is in said inactivated configuration;
      c) indexing means for preventing distal movement of said pin relative to said rivet when said pin has been moved within said bore to any one of several discrete positions relative to said rivet, said indexing means including
         i) a plurality of longitudinally spaced apart circumferential ridges positioned along said proximal portion of said pin, each ridge having an inclined proximal surface and a flat distal surface extending radially outward, and
         ii) a flat proximally facing stop wall positioned in said rivet, said distal surface of each ridge being resiliently engageable with said proximally facing stop wall to prevent distal movement of said pin relative to said rivet once said ridge is moved proximal to said stop wall, said inclined proximal surface of each said ridge permitting further proximal movement of said pin within said bore;
   C) placing the fastener so as to hold the soft tissue in contact with the bone; and
   D) moving the pin proximally to an indexed position to activate the rivet locking means.

17. The method of claim 16 wherein said locking means comprises at least two radially expandable legs projecting distally from said rivet.

18. The method of claim 17 wherein said legs have barbs for engaging bone.

19. The method of claim 18 wherein said fastener is fabricated from a resorbable material.

20. The method of claim 19 wherein said resorbable material comprises a polymer selected from the group consisting of polymers of lactide, glycolide, caprolactone, polyorthoesters, polydioxanone, trimethylene carbonate, polyethylene oxide or other resorbable polymer materials or blends of these respective polymers.

21. The method of claim 16 wherein said means for holding soft tissue comprises a plurality of soft tissue engaging barbs projecting distally from said rivet head.

22. The method of claim 17 wherein said flared portion at the distal portion of said pin is engageable with an inner surface of the rivet legs to expand said legs radially outward.

23. The method of claim 16 wherein said pin further includes a circumferential notch defining a proximal portion and a distal portion, said notch providing breaking means for separating said proximal portion from said distal portion when a pulling force of sufficient magnitude is applied to said proximal portion, and said method further includes the step applying to the proximal portion of said pin a pulling force of magnitude sufficient to break the pin at said notch.

24. A surgical fastener for securing soft tissue to bone comprising:
   a rivet having an axial bore, a proximal head portion, and a distal portion movable between an unexpanded position and an expanded position for receiving a flared portion of a setting pin, said rivet being composed of a resorbable material; and
   a setting pin slidably received in said bore, said setting pin having a flared distal portion to expand said distal portion of said rivet upon sliding movement of said setting pin, said setting pin being composed of a resorbable material, said surgical fastener further comprising indexing means for preventing distal movement of said setting pin relative to said rivet when said setting pin has been moved within said bore to any one of several discrete positions relative to said rivet, said indexing means including
      i) a plurality of longitudinally spaced apart circumferential ridges positioned along said proximal portion of said setting pin, each ridge having an inclined proximal surface and a flat distal surface extending radially outward, and
      ii) a flat proximally facing stop wall positioned in said rivet, said distal surface of each said ridge being resiliently engageable with said proximally facing stop wall to prevent distal movement of said setting pin relative to said rivet once said ridge is moved proximal to said stop wall, said inclined proximal surface of each said ridge permitting further proximal movement of said pin within said bore.

25. The fastener of claim 24, wherein sliding of said pin towards said head portion causes expansion of said distal portion of said rivet.

26. The fastener of claim 25, wherein said distal portion of said rivet comprises a plurality of resilient spaced apart legs.

27. The fastener of claim 26, wherein each of said legs has a plurality of barbs extending radially outwardly.

28. The fastener of claim 27, wherein said proximal head portion has a pair of distally projecting barbs.

29. The fastener of claim 28, wherein said pin further comprises a notch providing a breaking means for separating a proximal portion of said pin from said distal portion when a pulling force of sufficient magnitude is applied.

30. The fastener of claim 29, further comprising means for restricting movement of said pin, said restricting means comprising a narrowed portion formed in said bore and at least one circumferential rib formed on said pin.

31. The surgical fastener of claim 24 wherein said flared portion of said pin has a progressively greater diameter in the distal direction.

32. A surgical fastener for securing soft tissue to bone, which comprises:
(a) a rivet having an axial bore, distal locking means for frictionally engaging the bone to secure the rivet thereto, a proximal head portion integral to said rivet, and a plurality of tissue engaging barbs integral with said head portion, said barbs projecting distally from said head portion; and
(b) a pin receivable into said bore and proximally slidable therein, said pin having means for activating said rivet locking means in response to proximal movement of said pin with the bore,
said rivet locking means being movable between an inactivated configuration and an activated configuration, and said pin having an end portion distal to said rivet locking means when said rivet locking means is in said inactivated configuration.

33. The surgical fastener of claim 32 wherein said head portion has a flat proximal portion from which said barbs project.

* * * * *